United States Patent
Iwakata et al.

(10) Patent No.: US 11,872,366 B2
(45) Date of Patent: Jan. 16, 2024

(54) CONNECTING STRUCTURE FOR MEDICAL USE

(71) Applicant: KOYO SANGYO CO., LTD., Tokyo (JP)

(72) Inventors: Mario Iwakata, Niigata (JP); Hiroki Watanabe, Niigata (JP); Takayuki Miyazaki, Niigata (JP)

(73) Assignee: KOYO SANGYO CO., LTD., Tokyo (JP)

( * ) Notice: Subject to any disclaimer, the term of this patent is extended or adjusted under 35 U.S.C. 154(b) by 687 days.

(21) Appl. No.: 17/053,993

(22) PCT Filed: Aug. 15, 2019

(86) PCT No.: PCT/JP2019/032019
§ 371 (c)(1),
(2) Date: Nov. 9, 2020

(87) PCT Pub. No.: WO2020/070983
PCT Pub. Date: Apr. 9, 2020

(65) Prior Publication Data
US 2021/0085951 A1   Mar. 25, 2021

(30) Foreign Application Priority Data
Oct. 4, 2018 (JP) .................... 2018-188958

(51) Int. Cl.
*A61M 39/10*     (2006.01)
(52) U.S. Cl.
CPC . *A61M 39/1011* (2013.01); *A61M 2039/1033* (2013.01); *A61M 2039/1083* (2013.01);
(Continued)

(58) Field of Classification Search
CPC .............. A61M 39/1011; A61M 39/10; A61M 2039/1033; A61M 2039/1044;
(Continued)

(56) References Cited

U.S. PATENT DOCUMENTS

2008/0172039 A1   7/2008  Raines
2008/0287920 A1   11/2008 Fangrow et al.
(Continued)

FOREIGN PATENT DOCUMENTS

CN   106232173 A   12/2016
EP     3108926 A1  12/2016
(Continued)

OTHER PUBLICATIONS

Japan Patent Office, International Search Report for corresponding International Application No. PCT/JP2019/032019, dated Oct. 8, 2019.
(Continued)

*Primary Examiner* — Nathan R Price
*Assistant Examiner* — Sarah Dympna Grasmeder
(74) *Attorney, Agent, or Firm* — Jodi A. Reynolds, Esq.; Harter Secrest & Emery LLP (57) ABSTRACT

A connecting structure for medical use includes a male assembly 1 and a female connector 2. The male assembly 1 includes a male connector 10 and a threadedly engageable cylinder 20. A male luer portion 11 of the male connector 10 and a female luer portion 2a of the female connector 2 are joined by turning the threadedly engageable cylinder 20 in a tightening direction in a state where a female screw 21a of the threadedly engageable cylinder 20 and an engageable protrusion 2c of the female connector 2 are threadedly engaged with each other. A torque limiting mechanism 50 is disposed between an operation cylinder 30 mounted on an outer periphery of the threadedly engageable cylinder 20 and
(Continued)

the threadedly engageable cylinder 20. Engageable teeth 51 are formed in an inner periphery of one end portion of the operation cylinder 30 over an entire periphery. A slit 54 is formed in one end portion of the threadedly engageable cylinder 20. The slit is composed only of a straight portion extending from an end of the threadedly engageable cylinder in an axial direction. An area adjacent to the slit 54 is provided as an elastically deformable portion 52. A first engageable claw 53 engageable with the engageable teeth 51 is formed in the elastically deformable portion 52.

8 Claims, 11 Drawing Sheets (52) U.S. Cl.
 CPC ............... *A61M 2039/1088* (2013.01); *A61M 2205/0216* (2013.01)

(58) Field of Classification Search
 CPC ........... A61M 2205/0216; F16L 19/025; F16L 19/005; F16L 47/04; F16L 15/08; F16L 285/92
 See application file for complete search history.

(56) References Cited

U.S. PATENT DOCUMENTS

| | | | |
|---|---|---|---|
| 2013/0076030 A1* | 3/2013 | Fog | F16L 19/07 285/362 |
| 2014/0265312 A1 | 9/2014 | McAlister | |
| 2017/0120032 A1* | 5/2017 | Miyazaki | A61M 39/10 |
| 2018/0369559 A1 | 12/2018 | Iwakata et al. | |

FOREIGN PATENT DOCUMENTS

| | | |
|---|---|---|
| JP | S59-087840 | 6/1984 |
| JP | 2010-527276 A | 8/2010 |
| JP | 2013-208206 A | 10/2013 |
| WO | 02/096500 A1 | 12/2002 |
| WO | 2016157974 A1 | 10/2016 |
| WO | 2018189842 A1 | 10/2018 |

OTHER PUBLICATIONS

Japan Patent Office, International Preliminary Report on Patentability for corresponding International Application No. PCT/JP2019/032019, dated Apr. 15, 2021.

European Patent Office, Extended European Search Report for corresponding European patent application No. 19868858.2, dated Nov. 22, 2021.

Chinese Patent Office, Office Action dated Jan. 19, 2022 with the English translation.

* cited by examiner

CONNECTING STRUCTURE FOR MEDICAL USE

FIELD OF THE INVENTION

The present invention relates to a connecting structure for medical use for connecting medical components such as tubes.

BACKGROUND OF THE INVENTION

There are various types of connecting structures for medical use. A connecting structure for medical use of the kind disclosed in Patent Document 1 to be described later includes a male assembly and a female connector.

The male assembly includes a male connector and a threadedly engageable cylinder rotatably attached to the male connector. The male connector includes a male luer portion having a tapered outer periphery. The threadedly engageable cylinder includes a threadedly engageable portion disposed outside of the male luer portion in a radial direction. A female screw is formed in an inner periphery of the threadedly engageable portion.

The female connector includes a female luer portion having a tapered inner periphery. Engageable protrusions threadedly engageable with the female screw are formed in an outer periphery of a distal end portion of the female luer portion.

When the threadedly engageable cylinder is turned in a tightening direction in a state where the female screw of the threadedly engageable cylinder and the engageable protrusions of the female connector are threadedly engaged with each other, the male luer portion and the female luer portion are joined. When the threadedly engageable cylinder is turned further in the tightening direction, the male luer portion and the female luer portion are tightly joined with a pressing force working therebetween, providing sufficient sealing properties.

In the connecting structure for medical use of Patent Document 1, an excessive force may be applied to join the male luer portion and the female luer portion by excessive tightening by the threadedly engageable cylinder.

To solve the problem mentioned above, the inventors of the present application developed a connecting structure for medical use including a torque limiting mechanism as disclosed in Patent Document 2 to be described later.

The torque limiting mechanism is disposed between the threadedly engageable cylinder and an operation cylinder mounted on an outer periphery of the threadedly engageable cylinder. The torque limiting mechanism transmits a rotary torque of the operation cylinder in a tightening direction to the threadedly engageable cylinder. The torque limiting mechanism allows the operation cylinder to be turned idly with respect to the threadedly engageable cylinder when the rotary torque exceeds a predetermined torque. Thereby, the excessive tightening by the threadedly engageable cylinder can be prevented.

The torque limiting mechanism includes engageable teeth formed in the outer periphery of the threadedly engageable cylinder over an entire periphery and engageable claws formed in an inner periphery of an end portion of the operation cylinder, the engageable claws being engageable with the engageable teeth. A lot of slits extending in an axial direction from an end of the operation cylinder are formed in the end portion of the operation cylinder. Areas between the slits are provided as elastic leaves. The engageable claws are formed in the elastic leaves.

PRIOR ART DOCUMENT

Patent Document

Patent Document 1: Japanese Utility Model Application Publication No. S59-87840
Patent Document 2: International Patent Application Publication No. WO2016/157974
Patent Document 3: Japanese Patent Application Publication No. 2010-527276

SUMMARY OF THE INVENTION

Problem to be Solved by the Invention

In the connecting structure for medical use including the torque limiting mechanism disclosed in Patent Document 2, the torque limiting mechanism is not protected from dust. The elastic leaf including the engageable claw is defined on three sides by two slits and an end edge of the operation cylinder. Therefore, an elastic coefficient of the elastic leaf is relatively low, and the predetermined torque at which the operation cylinder starts the idle turning cannot be set adequately high according to necessity.

The connecting structure for medical use disclosed in FIGS. 73 to 75 of Patent Document 3 includes a loosening prevention mechanism disposed between a male connector and a threadedly engageable cylinder, but fails to include a torque limiting mechanism.

Means for Solving the Problems

To solve the problems mentioned above, the present invention provides a connecting structure for medical use including a male assembly and a female connector of a cylindrical configuration, the male assembly including a male connector of a cylindrical configuration and a threadedly engageable cylinder rotatably coupled to the male connector, the male connector including a male luer portion and a support portion arranged in a direction from a distal end to a basal end thereof in this order, the threadedly engageable cylinder including a threadedly engageable portion and a mounting portion arranged in a direction from a distal end to a basal end thereof in this order, the mounting portion rotatably mounted on an outer periphery of the support portion of the male connector, the threadedly engageable portion including a female screw in an inner periphery thereof, the threadedly engageable portion disposed outside of the male luer portion in a radial direction, the female connector including a female luer portion and an engageable protrusion formed in an outer periphery of the female luer portion, the male luer portion and the female luer portion joined by turning the threadedly engageable cylinder in a tightening direction in a state where the female screw of the threadedly engageable cylinder and the engageable protrusion of the female connector are threadedly engaged with each other, the connecting structure further including an operation cylinder mounted on an outer periphery of the threadedly engageable cylinder and a torque limiting mechanism disposed between the threadedly engageable cylinder and the operation cylinder, the torque limiting mechanism transmitting a rotary torque of the operation cylinder in a tightening direction to the threadedly engageable cylinder, the torque limiting mechanism allowing the operation cylinder to be turned idly with respect to the threadedly engageable cylinder when the rotary torque exceeds a predetermined torque, the torque limiting mechanism including engageable teeth formed in an inner periphery of one end portion of the operation cylinder in an axial direction over an entire periphery and at least one first engageable claw protruded outward in a radial direction from an outer surface of one end portion of the threadedly engageable cylinder in an axial direction, the first engageable claw engageable with the engageable teeth, wherein at least one slit is formed in the one end portion of the threadedly engageable cylinder, the slit composed only of a straight portion extending in the axial direction from an end of the threadedly engageable cylinder, at least one of two areas of the one end portion of the threadedly engageable cylinder adjacent to the slit in a circumferential direction is provided as an elastically deformable portion having a lower elastic coefficient than the other areas of the one end portion of the threadedly engageable cylinder, the first engageable claw is formed in an outer surface of the elastically deformable portion, and the elastically deformable portion is deformed inward in the radial direction when the operation cylinder is turned idly and the first engageable claw is moved over the engageable teeth.

According to the features mentioned above, the torque limiting mechanism that prohibits the excessive tightening by the threadedly engageable cylinder can be covered by the operation cylinder, thereby protecting the torque limiting mechanism from dust.

Furthermore, since the area adjacent to the slit composed only of the straight portion is provided as the elastically deformable portion, the torque (predetermined torque) at which the operation cylinder starts the idle turning can be set adequately high. It is because since the elastically deformable portion is defined on two sides by the slit and an end edge of the threadedly engageable cylinder, an elastic coefficient of the elastically deformable portion can be higher than that of an elastically deformable portion that is defined on three sides, for example.

Preferably, a dimension of the first engageable claw in the axial direction is shorter than that of the slit. According to the features mentioned above, a major portion of the engageable claw can be disposed in the area provided as the elastically deformable portion. Therefore, the engageable claw can be smoothly moved over the engageable teeth when the operation cylinder is turned idly.

A dimension of the engageable claw in the axial direction can be longer than the slit. In this case, the predetermined torque can be set higher.

Locations and the number of the engageable claws can be determined according to a required predetermined torque. Specifically, a predetermined torque is higher when the enageable claw is located spaced from the slit in a circumferential direction than when the engageable claw is located adjacent to the slit. The predetermined torque is increased as the number of the engageable claws is increased.

Preferably, a loosening prevention mechanism is disposed between the support portion of the male connector and the mounting portion of the threadedly engageable cylinder, the loosening prevention mechanism prohibiting the threadedly engageable cylinder from being rotated in a loosening direction with respect to the male connector in a state where the male luer portion and the female luer portion are joined;

the loosening prevention mechanism includes ratchet teeth formed in one of the support portion of the male connector and the mounting portion of the threadedly engageable cylinder over an entire periphery, at least one elastic leaf formed in the other of the support portion and the mounting portion and a second engageable claw formed in the elastic leaf and engageable with the ratchet teeth; and the elastic coefficient of the elastically deformable portion of the torque limiting mechanism is higher than an elastic coefficient of the elastic leaf of the loosening prevention mechanism.

According to the features mentioned above, the threadedly engageable cylinder is prohibited from being turned in the loosening direction with respect to the male connector in the state where the male luer portion and the female luer portion are joined. Therefore, sealing properties between the male luer portion and the female luer portion can be maintained, thereby surely preventing leakage of fluid. The loosening prevention mechanism does not interfere with actions of the torque limiting mechanism.

Preferably, the ratchet teeth of the loosening prevention mechanism are formed in an inner periphery of the mounting portion of the threadedly engageable cylinder, the ratchet teeth disposed adjacent to the elastically deformable portion of the torque limiting mechanism in the axial direction; the elastic leaf of the loosening prevention mechanism is formed in the support portion of the male connector; and the second engageable claw is protruded outward in the radial direction and engaged with the ratchet teeth.

Advantageous Effects of the Invention

According to the present invention, the torque limiting mechanism can be protected from dust. Furthermore, the torque (predetermined torque) at which the operation cylinder starts the idle turning can be set adequately high.

MODE FOR CARRYING OUT THE INVENTION

A connecting structure for medical use according to a first embodiment of the present invention will be described hereinafter with reference to FIGS. 1 to 10.

Figure 1:
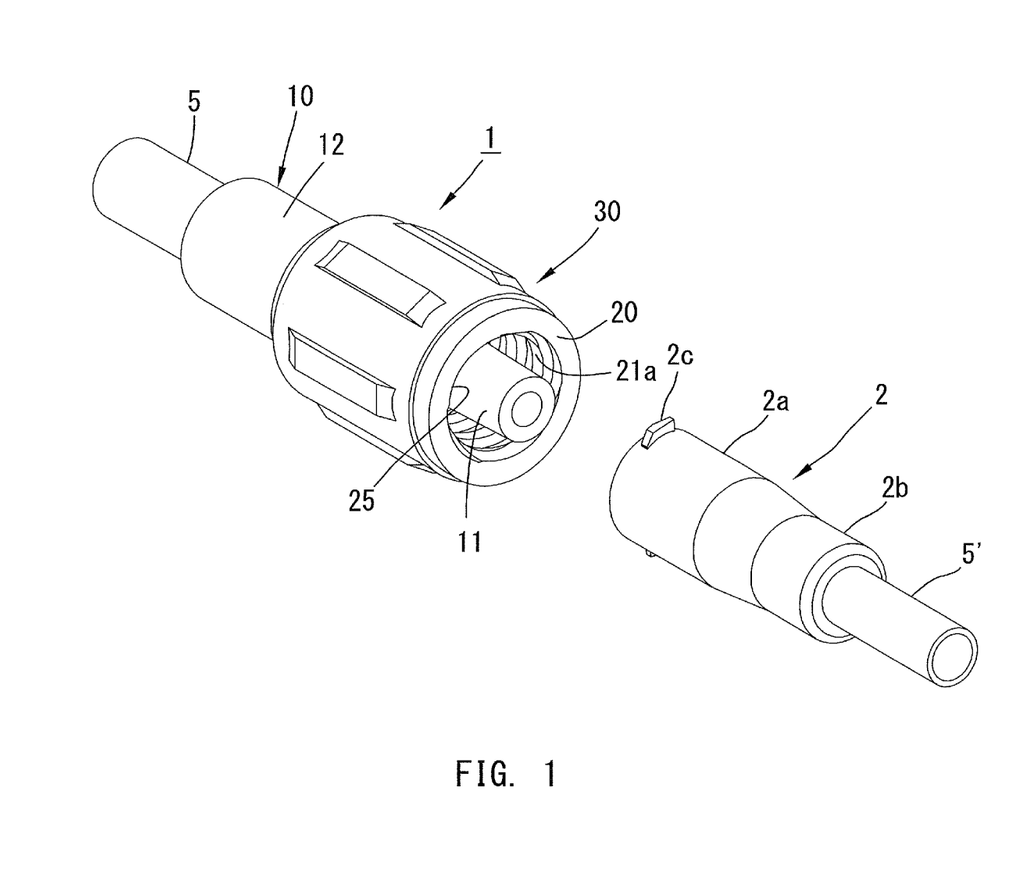
FIG. 1 is a perspective view of a connecting structure for medical use according to one embodiment of the present invention, with a male assembly and a female connector shown in a separate state.

As shown in FIG. 1, the connecting structure for medical use includes a male assembly 1 and a female connector 2. The male assembly 1 and the female connector 2 cooperate to connect tubes 5, 5' (first and second medical components) in which liquid such as medical solution and blood is to be flown. Components of the male assembly 1 and the female connector 2 are made of resin.

The female connector 2 having a simpler structure will be described first with reference to FIGS. 1 and 2B. The female connector 2 having a thin and long cylindrical configuration includes a female luer portion 2a in one end portion (distal end portion) thereof in an axial direction and a coupling portion 2b in the other end portion (basal end portion) thereof An inner surface of the female luer portion 2a has a gently tapered configuration whose diameter is gradually increased towards a distal end thereof. A pair of engageable protrusions 2c that work as male screws are formed in an outer periphery of a distal end portion of the female luer portion 2a 180 degrees apart from each other in a circumferential direction. An end portion of the tube 5' is to be inserted into and fixed at the coupling portion 2b.

Figure 2A:
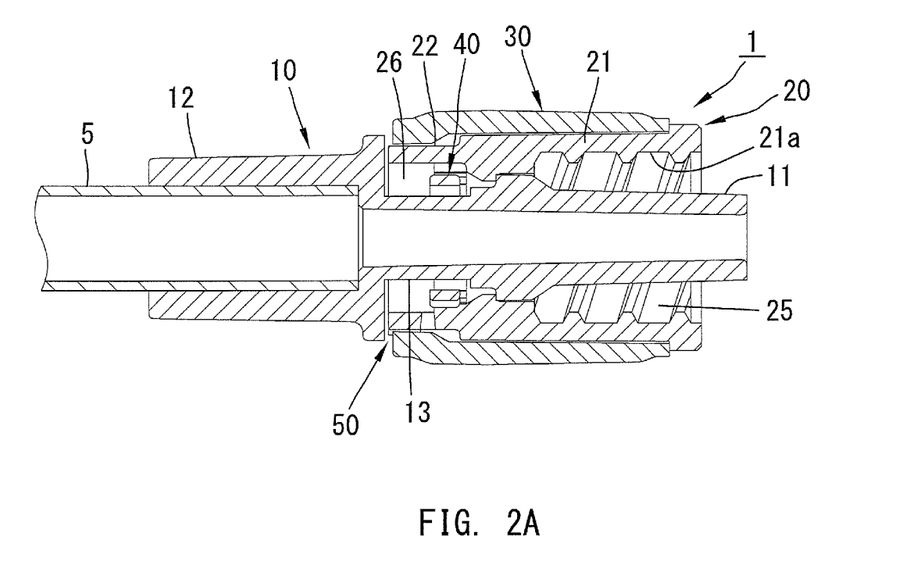
FIG. 2A is a longitudinal sectional view of the male assembly.
Figure 3:
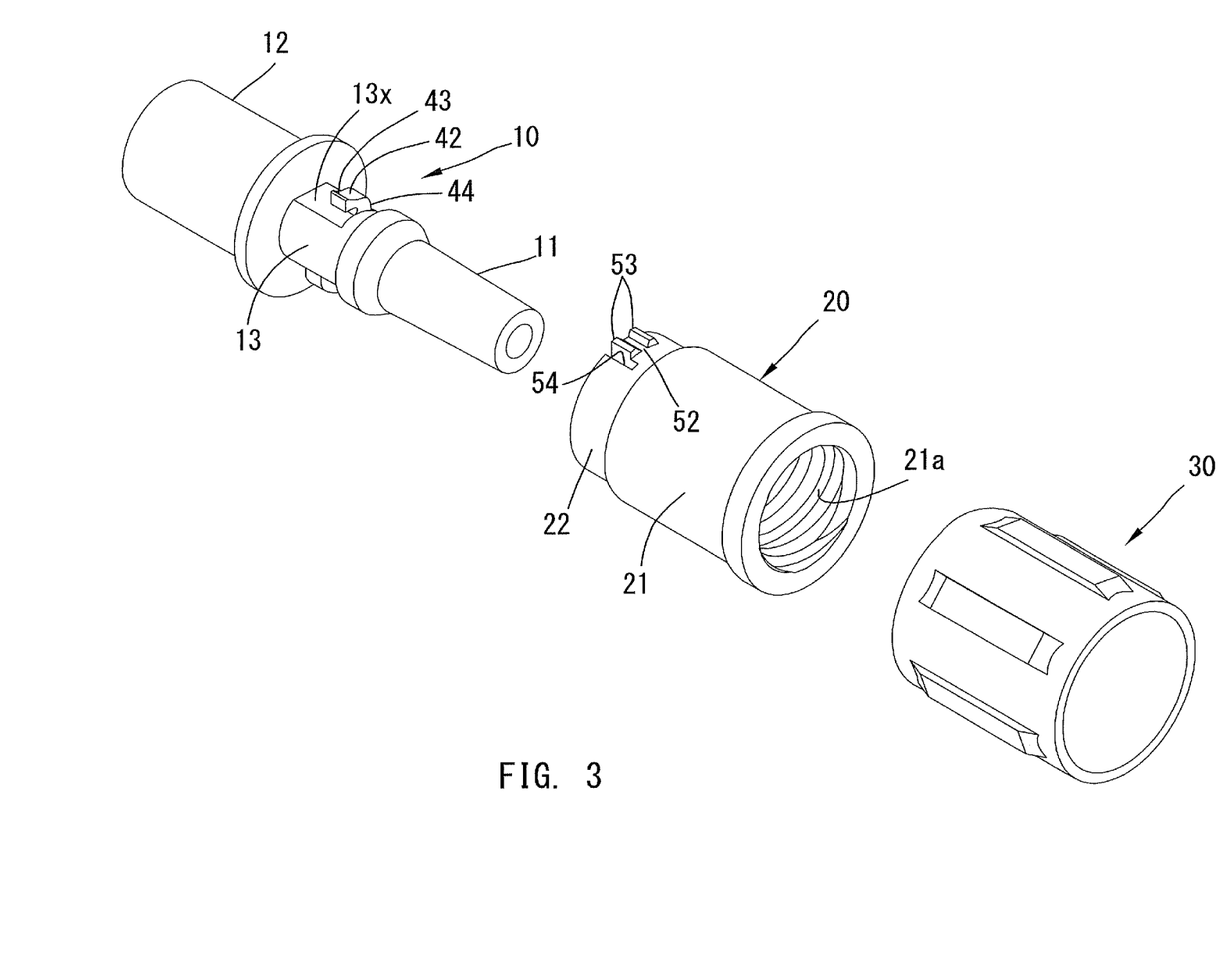
FIG. 3 is an exploded perspective view of the male assembly.
Figure 4:
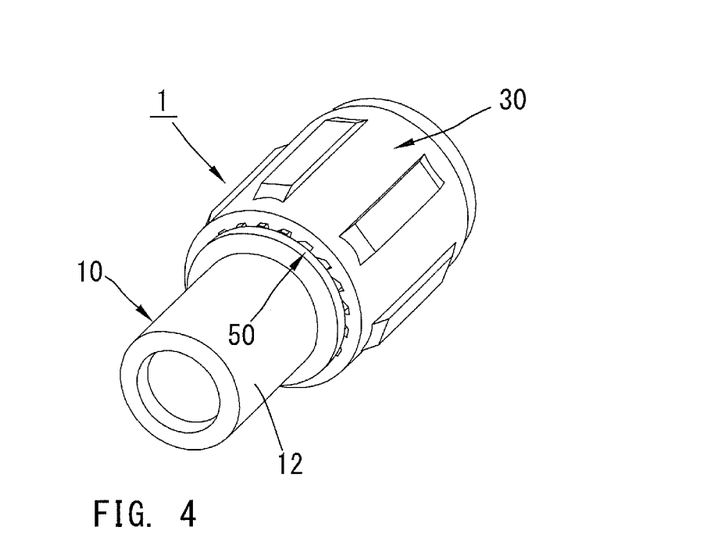
FIG. 4 is a perspective view of the male assembly, viewed from a different direction from that of FIG. 1.
Figure 5:
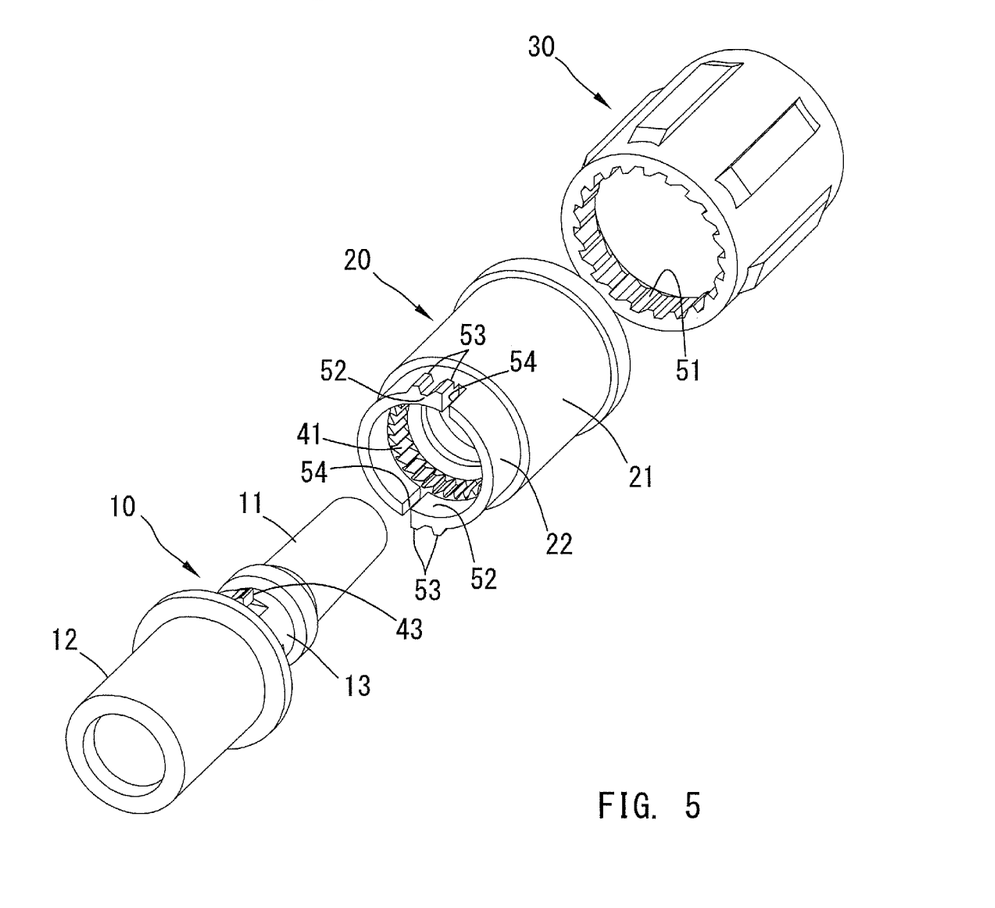
FIG. 5 is an exploded perspective view of the male assembly shown in FIG. 4.

As shown in FIGS. 2A, 3 and 5, the male assembly 1 includes a male connector 10, a threadedly engageable cylinder 20 and an operation cylinder 30. The threadedly engageable cylinder 20 is mounted on an outer periphery of the male connector 10 such that the threadedly engageable cylinder 20 is rotatable but immovable in an axial direction. The operation cylinder 30 is mounted on an outer periphery of the threadedly engageable cylinder 20 such that the operation cylinder 30 is rotatable but immovable in the axial direction.

Figure 6A:
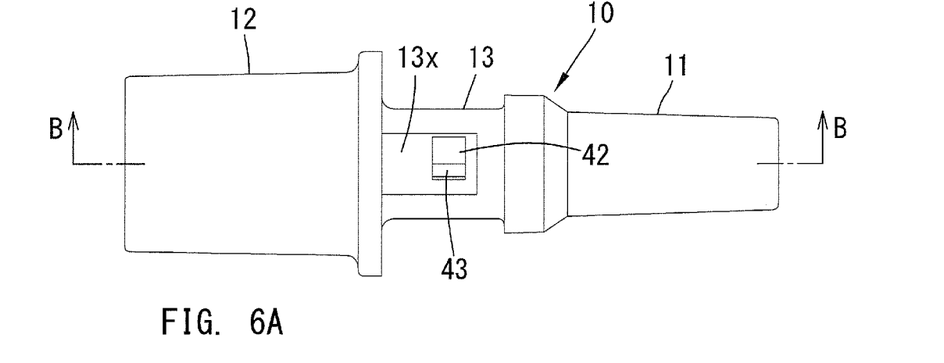
FIG. 6A is a plan view of a male connector of the male assembly.
Figure 6B:
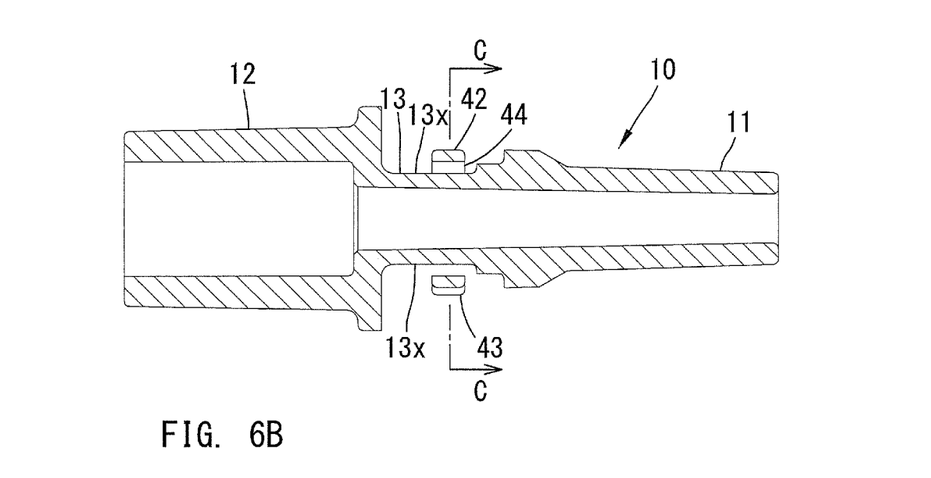
FIG. 6B is a cross-sectional view taken along line B-B of FIG. 6A.
Figure 6C:
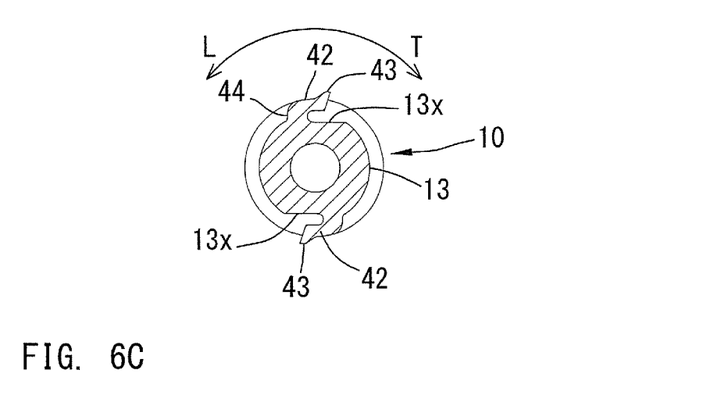
FIG. 6C is a cross-sectional view taken along line C-C of FIG. 6B.

As shown in FIG. 6, the male connector 10 has a thin and long cylindrical configuration. The male connector 10 includes a male luer portion 11 in one end portion (distal end portion) thereof in an axial direction, a coupling portion 12 in the other end portion (basal end portion) thereof and a support portion 13 in a middle portion thereof. An outer surface of the male luer portion 11 has a gently tapered configuration whose diameter is gradually reduced towards a distal end thereof. A taper angle of the outer surface of the male luer portion 11 and a taper angle of the inner surface of the female luer portion 2a are substantially the same. An end portion of the tube 5 is to be inserted into and fixed at the coupling portion 12.

Figure 7A:
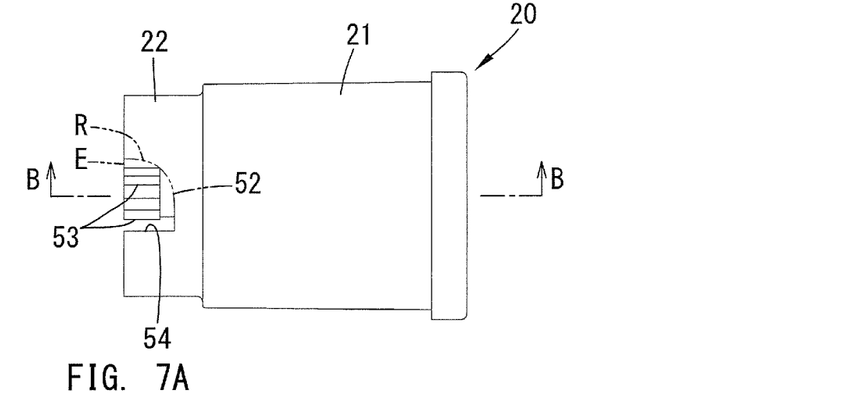
FIG. 7A is a plan view of a threadedly engageable cylinder of the male assembly.
Figure 7B:
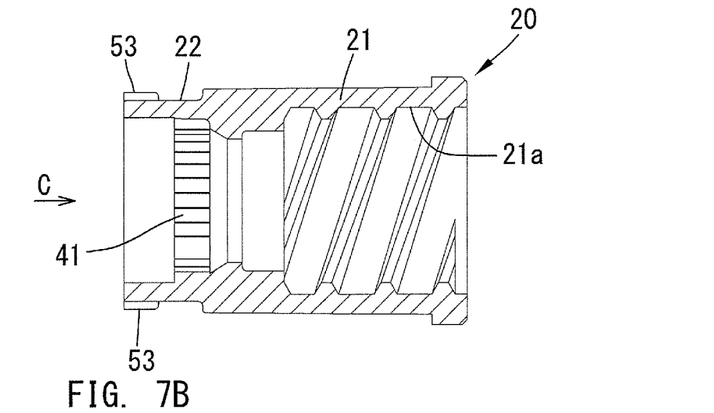
FIG. 7B is a cross-sectional view taken along line B-B of FIG. 7A.
Figure 7C:
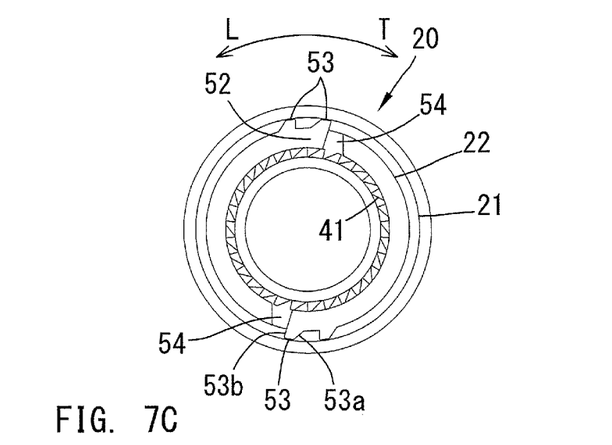
FIG. 7C is a view from direction C of FIG. 7B.

As shown in FIG. 7, the threadedly engageable cylinder 20 includes a threadedly engageable portion 21 in one end portion (distal end portion) thereof in the axial direction and a mounting portion 22 in the other end portion (basal end portion) thereof. A female screw 21a is formed in an inner periphery of the threadedly engageable portion 21. As shown in FIG. 2A, the mounting portion 22 is mounted on the support portion 13 of the male connector 10 such that the mounting portion 22 is rotatable but immovable in the axial direction.

As shown in FIGS. 1 and 2A, in a state where the threadedly engageable cylinder 20 is mounted on the male connector 10, the threadedly engageable portion 21 of the threadedly engageable cylinder 20 is disposed outside of the male luer portion 11 in a radial direction and an annular insertion space 25 is formed between the threadedly engageable portion 21 and the male luer portion 11. An annular gap 26 is formed between a small-diameter portion of the support portion 13 of the male connector 10 and the mounting portion 22 of the threadedly engageable cylinder 20.

As shown in FIG. 2A, the male assembly 1 includes a loosening prevention mechanism 40 disposed in the annular gap 26. The loosening prevention mechanism 40 includes ratchet teeth 41 and a pair of elastic leaves 42. As shown in FIGS. 5 and 7, the ratchet teeth 41 are formed in an inner periphery of the mounting portion 22 of the threadedly engageable cylinder 20 over an entire periphery. As shown in FIGS. 3 and 6, the elastic leaves 42 are formed in the small-diameter portion of the support portion 13 of the male connector 10.

Figure 10A:
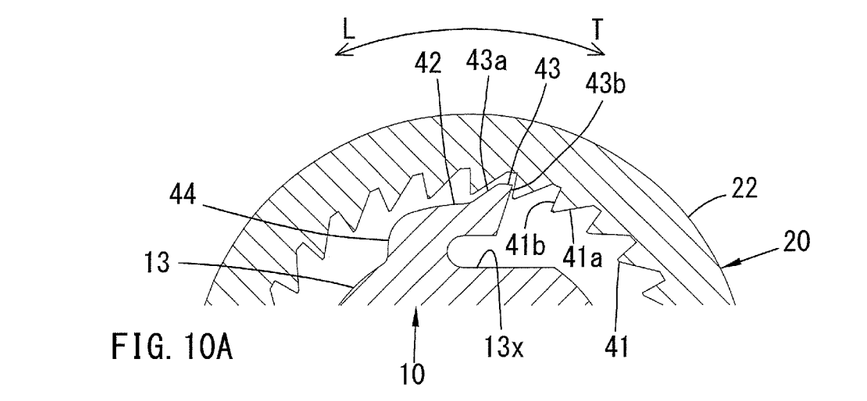
FIG. 10A is an enlarged cross-sectional view of a major portion of a loosening prevention mechanism of FIG. 9 in a state where a rotary torque is not applied to the threadedly engageable cylinder.

The ratchet teeth 41 are formed in the mounting portion 22 of the threadedly engageable cylinder 20 at a portion distanced away from a basal end of the mounting portion 22 through a predetermined distance. As shown in FIG. 10A, each tooth of the ratchet teeth 41 includes an inclined surface 41a on a tightening direction T side to be described later and a steep surface 41b on a loosening direction L side.

The small-diameter portion of the support portion 13 of the male connector 10 has a pair of chamfered flat surfaces 13x formed in an outer cylindrical periphery thereof. The pair of flat surfaces 13x are opposed to each other in the radial direction and extend parallel to each other.

A support protrusion 44 is protruded outward in the radial direction from an end portion of the flat surface 13x of the support portion 13 in a circumferential direction (end portion on the loosening direction L side). The elastic leaf 42 extends from a distal end of support protrusion 44 in the tightening direction T (circumferential direction) generally in parallel to the flat surface 13x. The support protrusion 44 and the elastic leaf 42 are arranged in a generally L-shaped configuration. The elastic leaf 42 is spaced from the flat surface 13x. An engageable claw 43 protruded outward in the radial direction is formed in a distal end (free end) of the elastic leaf 42.

Figure 9:
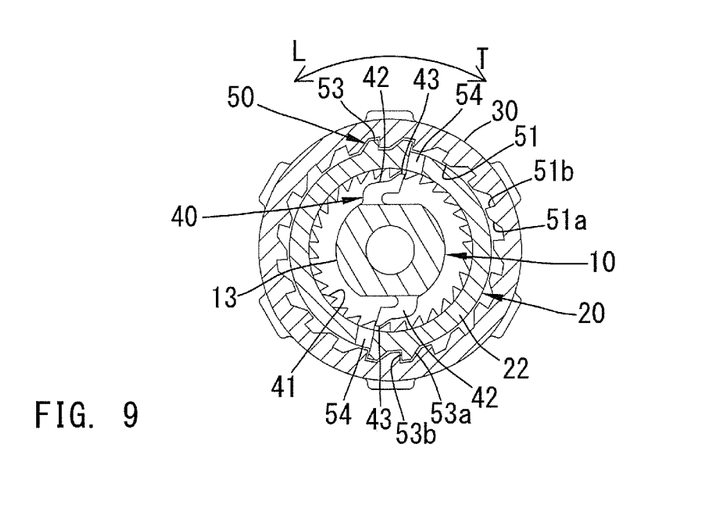
FIG. 9 is a cross-sectional view taken along line IX-IX of FIG. 2B.

As shown in FIGS. 9 and 10A, the pair of engageable claws 43 are engaged with the ratchet teeth 41. The engageable claw 43 includes an inclined surface 43a on the loosening direction L side and a steep surface 43b on the tightening direction T side. The inclined surface 43a of the engageable claw 43 is opposed to the inclined surface 41a of the corresponding tooth of the ratchet teeth 41 in the circumferential direction and the steep surfaces 41b, 43b are opposed to each other in the circumferential direction.

Figure 8A:
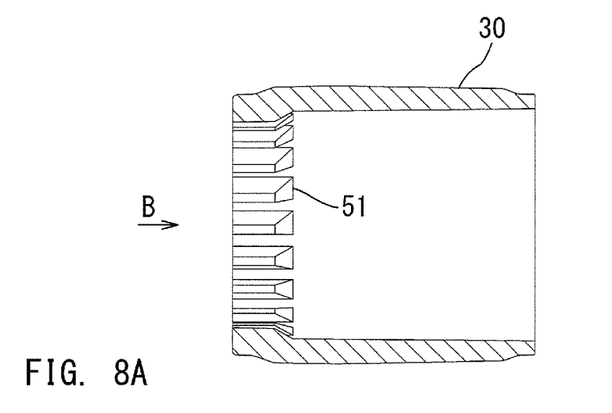
FIG. 8A is a longitudinal sectional view of an operation cylinder of the male assembly.
Figure 8B:
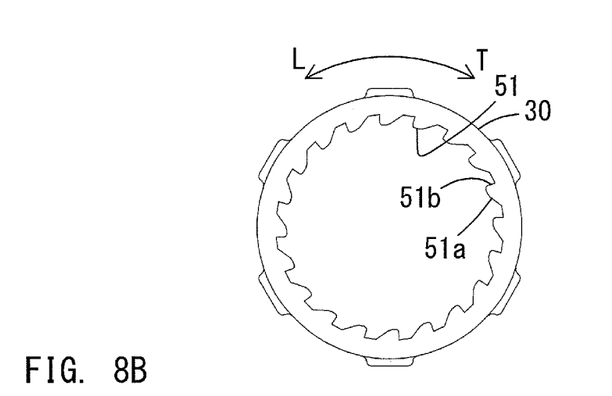
FIG. 8B is a view from direction B of FIG. 8A.

As shown in FIG. 2A, the male assembly 1 of this embodiment also includes a torque limiting mechanism 50 disposed between the threadedly engageable cylinder 20 and the operation cylinder 30. The torque limiting mechanism 50 includes engageable teeth 51 and a pair of elastically deformable portions 52. As shown in FIGS. 5 and 8, the engageable teeth 51 are formed in an inner periphery of a basal end portion of the operation cylinder 30 over an entire periphery. As shown in FIGS. 3, 5 and 7, the elastically deformable portions 52 are formed in the basal end portion of the threadedly engageable cylinder 20.

As shown in FIGS. 8 and 9, each tooth of the engageable teeth 51 includes an inclined surface 51a on the tightening direction T side and a steep surface 51b on the loosening direction L side as with the ratchet teeth 41 of the loosening prevention mechanism 40.

As shown in FIGS. 3, 5 and 7, a pair of slits 54 are formed in an end portion of the mounting portion 22 of the threadedly engageable cylinder 20 180 degrees apart from each other in the circumferential direction. The slit 54 composed only of a straight portion extending in the axial direction from an end of the mounting portion 22 has an I-shaped configuration. Elastic coefficients of areas adjacent to opposite sides of the slit 54 in the circumferential direction are lower than those of other areas of the end portion of the mounting portion 22. In this embodiment, the area of the end portion of the mounting portion 22 on the loosening direction L side of the slit 54 (area indicated by letter R in FIG. 7A) is provided as the elastically deformable portion 52. The elastically deformable portion 52 is disposed adjacent to the ratchet teeth 41 of the loosening prevention mechanism 40 in the axial direction. An elastic coefficient of the elastically deformable portion 52 is much higher than that of the elastic leaf 42 of the loosening prevention mechanism 40.

As shown in FIG. 7A, the elastically deformable portion 52 is defined on two sides only by the slit 54 composed only of the straight portion and an end edge E of the threadedly engageable cylinder 20. Therefore, the elastic coefficient of the elastically deformable portion 52 can be higher compared with when the elastically deformable portion 52 is defined on three sides, for example.

Each of the elastically deformable portions 52 has an engageable claw 53 formed in an outer surface thereof at a location adjacent to the slit 54. Another engageable claw 53 is formed at a location spaced from the engageable claw 53 in the circumferential direction through a distance corresponding to one pitch of the engageable teeth 51. The engageable claws 53 extend from the end edge E of the threadedly engageable cylinder 20 in the axial direction. Dimensions of the engageable claws 53 are shorter than the slits 54 in the axial direction.

As shown in FIG. 9, the engageable claws 53 are protruded outward in the radial direction and engaged with the engageable teeth 51. The engageable claw 53, as with the engageable claw 43 of the loosening prevention mechanism 40, includes an inclined surface 53a on the loosening direction L side and a steep surface 53b on the tightening direction T side. In an engaged state, the inclined surface 53a of the engageable claw 53 is opposed to the inclined surface 51a of the corresponding tooth of the engageable teeth 51 in the circumferential direction and the steep surfaces 51b, 53b are opposed to each other in the circumferential direction.

The female connector 2 is brought closer to the male assembly 1 having the features mentioned above and the male luer portion 11 is inserted into the female luer portion 2a. The insertion proceeds without resistance until the engageable protrusions 2c of the female connector 2 are abutted against the female screw 21a of the threadedly engageable cylinder 20 of the male assembly 1.

Next, when the operation cylinder 30 is turned in the tightening direction T, a torque of the operation cylinder 30 is transmitted to the threadedly engageable cylinder 20 via the torque limiting mechanism 50. Since the elastic coefficient of the elastically deformable portion 52 of the torque limiting mechanism 50 is high, the engageable claw 53 and corresponding tooth of the engageable teeth 51 are maintained in an engaged state with the inclined surface 53a of the engageable claw 53 and the inclined surface 51a of the corresponding tooth of the engageable teeth 51 abutted against each other. Therefore, the operation cylinder 30 and the threadedly engageable cylinder 20 are turned together.

Figure 10B:
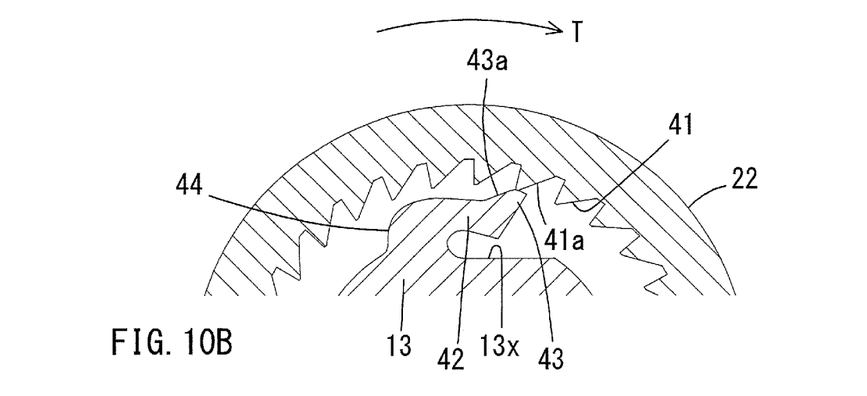
FIG. 10B is an enlarged cross-sectional view of the major portion of the loosening prevention mechanism in a state where a rotary torque in a tightening direction is applied to the threadedly engageable cylinder.

As mentioned above, when the threadedly engageable cylinder 20 is turned in the tightening direction T, the inclined surfaces 43a of the engageable claws 43 of the loosening prevention mechanism 40 slide on the inclined surfaces 41a of the ratchet teeth 41 as shown in FIG. 10B. Therefore, the engageable claws 43 can be moved over the ratchet teeth 41 of the threadedly engageable cylinder 20. Since this movement is accompanied by an elastic deformation of the elastic leaf 42 inward in the radial direction, the threadedly engageable cylinder 20 can be turned with respect to the male connector 10 without receiving much resistance from the loosening prevention mechanism 40.

By turning the threadedly engageable cylinder 20 in the tightening direction T as mentioned above, the threaded engagement between the female screw 21a and the engageable protrusions 2c proceeds, and the male luer portion 11 and the female luer portion 2a are joined with a pressing force working therebetween. Thereby, the male luer portion 11 and the female luer portion 2a can be joined with sufficient sealing properties. In this condition, as shown in FIG. 2B, a surface 21x on a deeper side of a screw thread of the female screw 21a of the threadedly engageable cylinder 20 is abutted against the engageable protrusion 2c of the female connector 2.

When the operation cylinder 30 is turned further, it encounters a strong resistance from a portion where the male luer portion 11 and the female luer portion 2a are joined, and a rotary torque exceeds a predetermined torque. Then, the inclined surfaces 53a of the engageable claws 53 slide on the inclined surfaces 51a of the engageable teeth 51, and the engageable claws 53 are moved over the engageable teeth 51 of the operation cylinder 30 accompanied by elastic deformations of the elastically deformable portions 52 inward in the radial direction. Since the operation cylinder 30 is turned idly with respect to the threadedly engageable cylinder 20 as mentioned above, the rotary torque of the operation cylinder 30 is not transmitted to the threadedly engageable cylinder 20. Therefore, an excessive torque is not imparted to the threadedly engageable cylinder 20, thereby preventing the pressing force between the male luer portion 11 and the female luer portion 2a from becoming excessive. As a result, breakage of the male luer portion 11 and the female luer portion 2a can be prevented, and the male luer portion 11 and the female luer portion 2a can be prevented from being inseparably locked with each other.

Figure 10C:
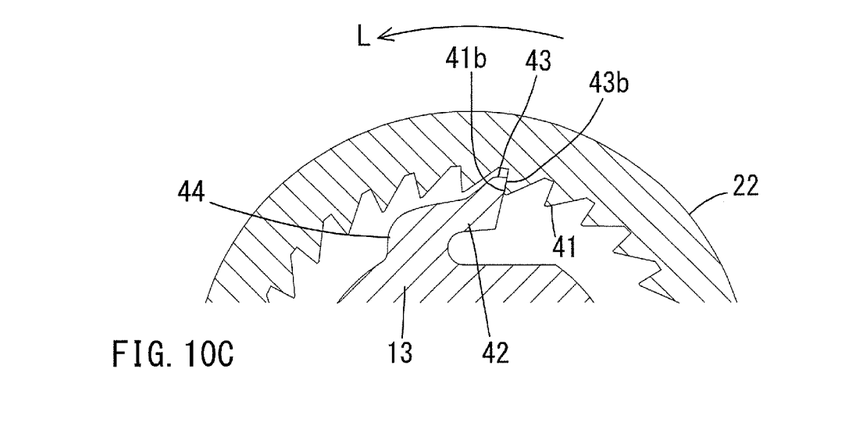
FIG. 10C is an enlarged cross-sectional view of the major portion of the loosening prevention mechanism in a state where a rotary torque in a loosening direction is applied to the threadedly engageable cylinder.

As shown in FIG. 10C, even when an unintentional torque in the loosening direction L is applied to the threadedly engageable cylinder 20 in the joined condition mentioned above, the threadedly engageable cylinder 20 is prohibited from being rotated in the loosening direction with respect to the male connector 10. It is because the steep surfaces 43b of the engageable claws 43 catch the steep surfaces 41b of the corresponding teeth of the ratchet teeth 41.

Figure 2B:
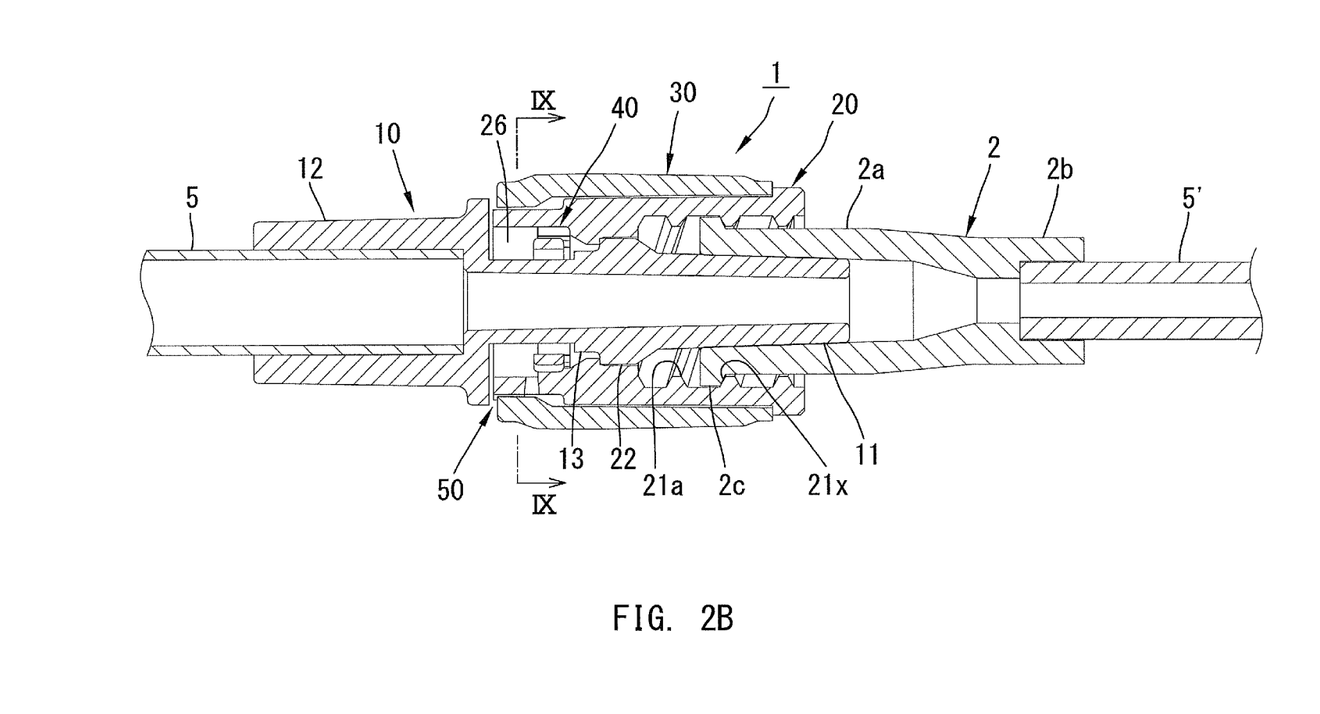
FIG. 2B is a longitudinal sectional view of the connecting structure for medical use, with the male assembly and the female connector shown in a joined state.

Since the threadedly engageable cylinder 20 is not rotated in the loosening direction with respect to the male connector 10 after the joining of the male luer portion 11 and the female luer portion 2a is completed as mentioned above, the surface 21x on the deeper side of the screw thread of the female screw 21a of the threadedly engageable cylinder 20 is maintained in the abutted state against the engageable protrusions 2c of the female connector 2 as shown in FIG. 2B. As a result, the female luer portion 2a and the male luer portion 11 are not displaced in a direction away from each other even when a pressure of fluid is high, and sufficient sealing properties can be maintained. Thereby, leakage of the fluid can be prohibited.

To disconnect the tubes 5, 5' after connecting them in this manner, the operation cylinder 30 is turned in the loosening direction L. Then, in the torque limiting mechanism 50, the steep surfaces 53b of the engageable claws 53 of the threadedly engageable cylinder 20 are abutted against the steep surfaces 51b of the corresponding teeth of the engageable teeth 51 of the operation cylinder 30, and the threadedly engageable cylinder 20 is rotated in the loosening direction together with the operation cylinder 30. At the same time, in the loosening prevention mechanism 40, the steep surfaces 43b of the engageable claws 43 of the male connector 10 are abutted against the steep surfaces 41b of the corresponding teeth of the ratchet teeth 41 of the threadedly engageable cylinder 20, and the male connector 10 is also rotated together with the threadedly engageable cylinder 20. As a result, the male luer portion 11 and the female luer portion 2b are released from the joined state.

Since the torque limiting mechanism 50 is covered with the operation cylinder 30, entrance of dust into the torque limiting mechanism 50 can be constrained.

Since the elastically deformable portion 52 of the torque limiting mechanism 50 is adjacent to the slit 54 composed only of the straight portion and has a high elastic coefficient as mentioned above, the torque (predetermined torque) at which the operation cylinder 30 starts the idle turning can be set adequately high.

Since the engageable claw 53 is shorter than the slit 54 in the axial direction, an entirety or a majority of the engageable claw 53 can be disposed in the area of the elastically deformable portion 52. Therefore, when the torque of the operation cylinder 30 exceeds the predetermined torque, the operation cylinder 30 can be smoothly turned idly.

The predetermined torque of the torque limiting mechanism 50 can be adjusted by changing locations and the number of the engageable claws 53. Modification examples will be described hereinafter with reference to FIGS. 11 to 13. Same reference numerals are used to designate parts that correspond to those in the first embodiment, and description thereof will be omitted.

Figure 11:
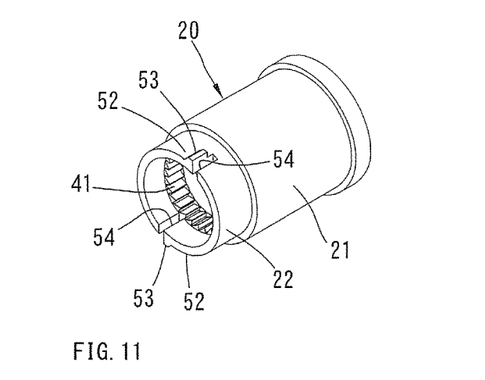
FIG. 11 is a perspective view of a modification example of the threadedly engageable cylinder.

FIG. 11 shows a modification in which only one engageable claw 53 is disposed adjacent to a slit 54 in each of elastically deformable portions 52. In this case, a predetermined torque is lower than the one in the first embodiment.

Figure 12:
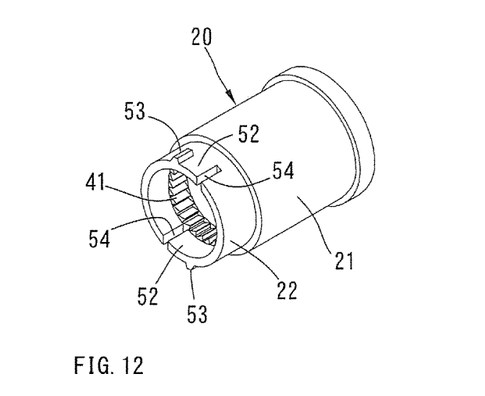
FIG. 12 is a perspective view of another modification example of the threadedly engageable cylinder.

FIG. 12 shows a modification in which only one engageable claw 53 is disposed spaced from a slit 54 in each of elastically deformable portions 52. In this case, a predetermined torque is higher than the one in the modification of FIG. 11 but lower than the one in the first embodiment.

Figure 13:
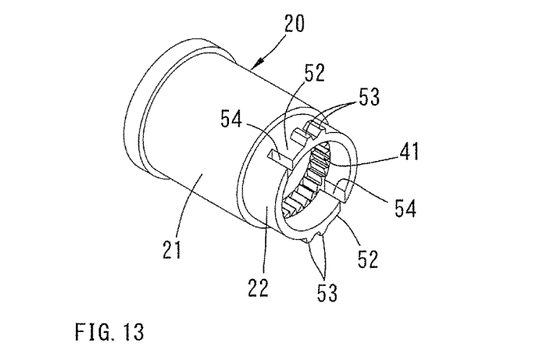
FIG. 13 is a perspective view of still another modification example of the threadedly engageable cylinder.

FIG. 13 shows a modification in which two engageable claws 53 are disposed spaced from a slit 54 in each of elastically deformable portions 52. In this case, a predetermined torque is higher than the one in the first embodiment. In FIG. 13, an area adjacent to the slit 54 on a tightening direction side is provided as the elastically deformable portion 52.

In the embodiment mentioned above, when a torque exceeds the predetermined torque and an operation cylinder 30 is turned idly in a process of turning the operation cylinder 30 in the tightening direction, it is mostly the elastically deformable portion 52 that is elastically deformed, and an elastic deformation of a threadedly engageable cylinder 20 as a whole and/or the operation cylinder 30 as a whole is relatively small.

Figure 14:
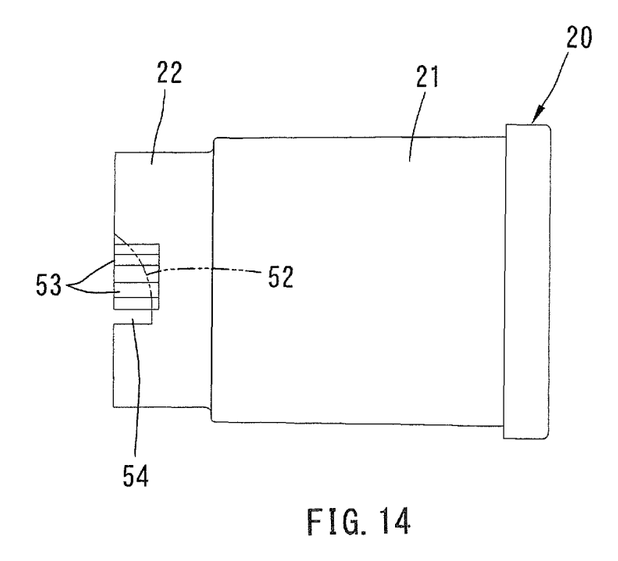
FIG. 14 is a plan view of yet another modification example of the threadedly engageable cylinder.

FIG. 14 shows a modification in which an engageable claw 53 is longer than a slit 54 in an axial direction, and therefore, a portion of the engageable claw 53 is located out of an elastically deformable portion 52. In this configuration, when an operation cylinder 30 is turned in a tightening direction and a torque exceeds a predetermined torque, it is not only the elastically deformable portion 52 that is elastically deformed. A threadedly engageable cylinder 20 as a whole and/or the operation cylinder 30 as a whole is elastically deformed. Therefore, the predetermined torque can be set high.

The present invention is not limited to the embodiments described above and various modifications can be made.

The loosening prevention mechanism may be omitted.

In the torque limiting mechanism, areas in opposite sides of the slit in the circumferential direction may be provided as the elastically deformable portions.

The support portion and the coupling portion of the male connector may be separate from each other and rotatable with respect to each other.

The present invention may be applied for connecting a three-way stopcock and a tube. The present invention may be applied for connecting various kinds of medical components.

INDUSTRIAL APPLICABILITY

The present invention may be applied to connecting structures for medical use.

The invention claimed is:
1. A connecting structure for medical use comprising:
a male assembly; and
a female connector of a cylindrical configuration,
the male assembly including a male connector of a cylindrical configuration and a threadedly engageable cylinder rotatably coupled to the male connector,
the male connector including a male luer portion and a support portion arranged in a direction from a distal end to a basal end thereof in this order,
the threadedly engageable cylinder including a threadedly engageable portion and a mounting portion arranged in a direction from a distal end to a basal end thereof in this order, the mounting portion rotatably mounted on an outer periphery of the support portion of the male connector, the threadedly engageable portion including a female screw in an inner periphery thereof, the threadedly engageable portion disposed outside of the male luer portion in a radial direction,
the female connector including a female luer portion and an engageable protrusion formed in an outer periphery of the female luer portion,
the male luer portion and the female luer portion joined by turning the threadedly engageable cylinder in a tightening direction in a state where the female screw of the threadedly engageable cylinder and the engageable protrusion of the female connector are threadedly engaged with each other, the connecting structure further comprising an operation cylinder mounted on an outer periphery of the threadedly engageable cylinder and a torque limiting mechanism disposed between the threadedly engageable cylinder and the operation cylinder;

the torque limiting mechanism transmitting a rotary torque of the operation cylinder in a tightening direction to the threadedly engageable cylinder;

the torque limiting mechanism allowing the operation cylinder to be turned idly with respect to the threadedly engageable cylinder when the rotary torque exceeds a predetermined torque;

the torque limiting mechanism including engageable teeth formed in an inner periphery of one end portion of the operation cylinder in an axial direction over an entire periphery and at least one first engageable claw protruded outward in a radial direction from an outer surface of one end portion of the threadedly engageable cylinder in an axial direction, the first engageable claw engageable with the engageable teeth; wherein at least one slit is formed in the one end portion of the threadedly engageable cylinder, the slit composed only of a straight portion extending in the axial direction from an end of the threadedly engageable cylinder;

at least one of two areas of the one end portion of the threadedly engageable cylinder adjacent to the slit in a circumferential direction is provided as an elastically deformable portion having a lower elastic coefficient than the other areas of the one end portion of the threadedly engageable cylinder;

the first engageable claw is formed in an outer surface of the elastically deformable portion; and the elastically deformable portion is deformed inward in the radial direction when the operation cylinder is turned idly and the first engageable claw is moved over the engageable teeth.

2. The connecting structure for medical use according to claim 1, wherein a dimension of the first engageable claw in the axial direction is shorter than that of the slit.

3. The connecting structure for medical use according to claim 1, wherein a dimension of the first engageable claw in the axial direction is longer than that of the slit.

4. The connecting structure for medical use according to claim 1, wherein the first engageable claw is disposed adjacent to the slit.

5. The connecting structure for medical use according to claim 1, wherein the first engageable claw is disposed spaced from the slit in the circumferential direction.

6. The connecting structure for medical use according to claim 1, wherein the first engageable claws are disposed at a location adjacent to the slit and at a location spaced from the slit in the circumferential direction.

7. The connecting structure for medical use according to claim 1, wherein:

a loosening prevention mechanism is disposed between the support portion of the male connector and the mounting portion of the threadedly engageable cylinder, the loosening prevention mechanism prohibiting the threadedly engageable cylinder from being rotated in a loosening direction with respect to the male connector in a state where the male luer portion and the female luer portion are joined;

the loosening prevention mechanism includes ratchet teeth formed in one of the support portion of the male connector and the mounting portion of the threadedly engageable cylinder over an entire periphery, at least one elastic leaf formed in the other of the support portion and the mounting portion and a second engageable claw formed in the elastic leaf and engageable with the ratchet teeth; and the elastic coefficient of the elastically deformable portion of the torque limiting mechanism is higher than an elastic coefficient of the elastic leaf of the loosening prevention mechanism.

8. The connecting structure for medical use according to claim 7, wherein:

the ratchet teeth of the loosening prevention mechanism are formed in an inner periphery of the mounting portion of the threadedly engageable cylinder, the ratchet teeth disposed adjacent to the elastically deformable portion of the torque limiting mechanism in the axial direction;

the elastic leaf of the loosening prevention mechanism is formed in the support portion of the male connector; and the second engageable claw is protruded outward in the radial direction and engaged with the ratchet teeth.

* * * * *